(12) United States Patent
Meguro et al.

(10) Patent No.: US 11,744,446 B2
(45) Date of Patent: Sep. 5, 2023

(54) MEDICAL DEVICE AND ENDOSCOPE SYSTEM

(71) Applicant: OLYMPUS CORPORATION, Tokyo (JP)

(72) Inventors: Chikayoshi Meguro, Hachioji (JP); Takuto Yoshinaga, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 471 days.

(21) Appl. No.: 17/065,898

(22) Filed: Oct. 8, 2020

(65) Prior Publication Data
US 2021/0022587 A1 Jan. 28, 2021

Related U.S. Application Data

(63) Continuation of application No. PCT/JP2019/006819, filed on Feb. 22, 2019.

(30) Foreign Application Priority Data

Apr. 16, 2018 (JP) .................................. 2018-078684

(51) Int. Cl.
*A61B 1/005* (2006.01)
*A61B 1/00* (2006.01)
*A61B 1/012* (2006.01)

(52) U.S. Cl.
CPC ........ *A61B 1/0052* (2013.01); *A61B 1/00066* (2013.01); *A61B 1/00128* (2013.01); *A61B 1/0125* (2013.01)

(58) Field of Classification Search
CPC .. A61B 1/0052; A61B 1/0125; A61B 1/00128
See application file for complete search history.

(56) References Cited

U.S. PATENT DOCUMENTS

| | | | | |
|---|---|---|---|---|
| 3,643,653 | A * | 2/1972 | Takahashi | A61B 1/07 600/129 |
| 4,586,491 | A * | 5/1986 | Carpenter | A61B 1/018 600/113 |
| 4,947,828 | A * | 8/1990 | Carpenter | A61B 1/07 600/113 |
| 4,979,496 | A * | 12/1990 | Komi | A61B 1/018 600/113 |
| 10,709,314 | B2 * | 7/2020 | Galperin | A61B 17/00234 |

(Continued)

FOREIGN PATENT DOCUMENTS

| | | |
|---|---|---|
| JP | H4-124101 U | 11/1992 |
| JP | H7-21003 U | 4/1995 |

(Continued)

OTHER PUBLICATIONS

International Search Report dated Apr. 16, 2019 issued in PCT/JP2019/006819.

*Primary Examiner* — Matthew J Kasztejna
(74) *Attorney, Agent, or Firm* — Scully, Scott, Murphy & Presser, P.C.

(57) ABSTRACT

A medical device includes an operation portion, an insertion portion that is insertable into a treatment instrument insertion channel of a mother endoscope, and a mounting portion provided at an operation portion to detachably mount the operation portion onto a bending operation member of the mother endoscope.

20 Claims, 5 Drawing Sheets

(56) References Cited

U.S. PATENT DOCUMENTS

| | | |
|---|---|---|
| 2016/0089008 A1 | 3/2016 | Simmons et al. |
| 2020/0146537 A1* | 5/2020 | Harada .............. A61B 1/00098 |
| 2020/0214542 A1* | 7/2020 | Yoshinaga ......... A61B 1/00133 |
| 2021/0016060 A1* | 1/2021 | Levasseur .......... A61B 1/00124 |
| 2022/0354343 A1* | 11/2022 | Brechbiel ............ A61B 1/0052 |

FOREIGN PATENT DOCUMENTS

| | | |
|---|---|---|
| JP | 5864496 B2 | 2/2016 |
| WO | WO 2016/053754 A1 | 4/2016 |

* cited by examiner

MEDICAL DEVICE AND ENDOSCOPE SYSTEM

CROSS REFERENCE TO RELATED APPLICATION

This application is a continuation application of PCT/JP2019/006819 filed on Feb. 22, 2019 and claims benefit of Japanese Application No. 2018-078684 filed in Japan on Apr. 16, 2018, the entire contents of which are incorporated herein by this reference.

BACKGROUND OF THE INVENTION

1. Field of the Invention

The present invention relates to a medical device that is insertable into a treatment instrument insertion channel of a first endoscope, and an endoscope system including the medical device and the first endoscope.

2. Description of the Related Art

Conventionally, a mother-baby endoscope system including a mother endoscope and a baby endoscope that is inserted into a treatment instrument insertion channel of the mother endoscope has been practically used as an endoscope for observation and medical treatment of, for example, inside of a bile duct or a pancreatic duct.

The mother endoscope in the mother-baby endoscope system is, for example, a duodenum side-view endoscope, and the baby endoscope is an endoscope that has a small diameter and is inserted into the treatment instrument insertion channel of the mother endoscope. The baby endoscope is protruded into a body cavity through a distal end portion of the mother endoscope inserted into a duodenum, and only the baby endoscope is selectively inserted into the bile duct or the pancreatic duct through a duodenal papilla to perform observation or medical treatment of the inside of the bile duct or the pancreatic duct.

FIG. 31 in Japanese Patent No. 5864496 illustrates, as an example of such a mother-baby endoscope, a configuration in which an operation portion of the baby endoscope is coupled on a distal end side of a biopsy port of the mother endoscope by using a strap and an insertion portion of the baby endoscope is looped and inserted through the biopsy port of the mother endoscope.

SUMMARY OF THE INVENTION

A medical device according to an aspect of the present invention is a medical device that is insertable into a treatment instrument insertion channel of a first endoscope including a first operation portion, a first insertion portion including a first bending portion and continuously provided on a distal end side of the first operation portion, a bending operation member for performing a bending operation of the first bending portion, the bending operation member being provided at a predetermined position of the first operation portion, and the treatment instrument insertion channel having a base end side opening in a region on the distal end side of the predetermined position of the first operation portion at which the bending operation member is provided and having a distal end side opening at a distal end portion of the first insertion portion. The medical device includes a second operation portion, a second insertion portion that is continuously provided on the distal end side of the second operation portion and is insertable into the treatment instrument insertion channel, and a mounting portion provided at the second operation portion to detachably mount the second operation portion onto the bending operation member.

An endoscope system according to another aspect of the present invention includes a first endoscope, and a medical device that is attachable to the first endoscope. The first endoscope includes a first operation portion, a first insertion portion including a first bending portion and continuously provided on a distal end side of the first operation portion, a bending operation member for performing a bending operation of the first bending portion, the bending operation member being provided at a predetermined position of the first operation portion, and a treatment instrument insertion channel having a base end side opening in a region on the distal end side of the predetermined position of the first operation portion at which the bending operation member is provided and having a distal end side opening at a distal end portion of the first insertion portion. The medical device includes a second operation portion, a second insertion portion that is continuously provided on the distal end side of the second operation portion and is insertable into the treatment instrument insertion channel, and a mounting portion provided at the second operation portion to detachably mount the second operation portion onto the bending operation member.

DETAILED DESCRIPTION OF THE PREFERRED EMBODIMENTS

Figure 1:
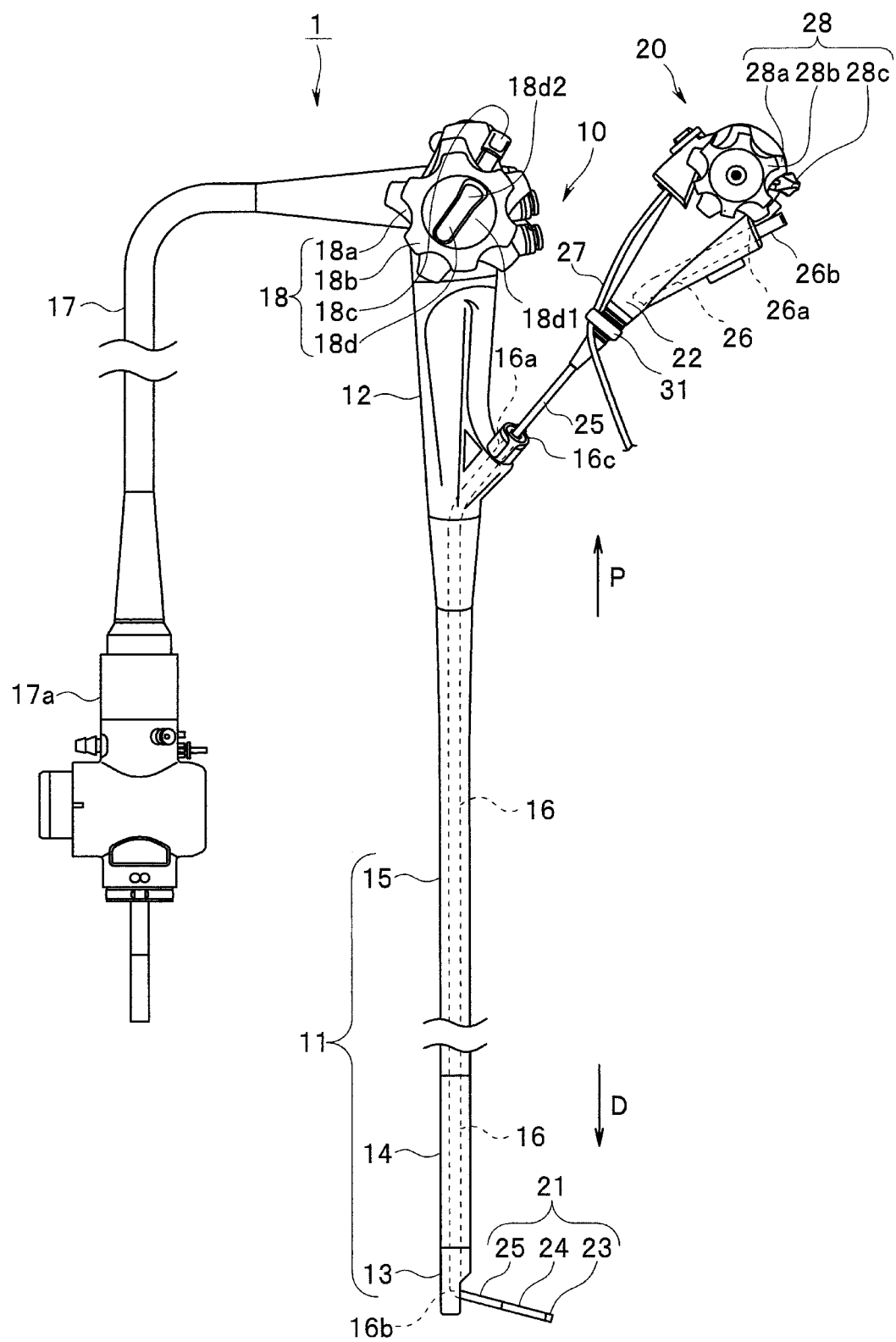
FIG. 1 is a front view illustrating a configuration of an endoscope system in Embodiment 1 of the present invention.

Embodiments of the present invention will be described below with reference to the accompanying drawings.

Note that, in each drawing used in the description below, scaling is sometimes different for each component so that the component has a size with which the component is recognizable in the drawing, and the present invention is not limited to the number of components, shapes of the components, ratios of sizes of the components, and the relative positional relation among the components illustrated in the drawings.

Embodiment 1

FIGS. 1 to 5 illustrate Embodiment 1 of the present invention, and FIG. 1 is a front view illustrating a configuration of an endoscope system 1. Note that, in FIG. 1 and the like, an arrow P indicates a base end side (proximal end direction) and an arrow D indicates a distal end side (distal end direction).

The endoscope system 1 of the present embodiment is configured as a mother-baby endoscope system including a mother endoscope 10 and a baby endoscope 20 as a medical device that is insertable into a treatment instrument insertion channel 16 of the mother endoscope 10. Note that, in the present embodiment, the medical device that is insertable into the treatment instrument insertion channel 16 of the mother endoscope 10 is, for example, the baby endoscope 20, but is not limited thereto but may be a treatment instrument such as forceps.

The mother endoscope 10 includes an insertion portion 11 that has an elongated shape and is inserted into an object, and an operation portion 12 continuously provided on the base end side of the insertion portion 11. The mother endoscope 10 is a first endoscope, the insertion portion 11 is a first insertion portion, and the operation portion 12 is a first operation portion. Various operation members necessary for operating the mother endoscope 10 are disposed at the operation portion 12.

The insertion portion 11 is configured by a distal end portion body 13, a bending portion 14, and a flexible tube portion 15 continuously and sequentially provided from the distal end side toward the base end side.

Although not illustrated, an illumination optical system configured to emit illumination light transmitted by, for example, a light guide bundle, and an image pickup unit including an objective optical system and an image sensor are disposed at the distal end portion body 13 of the insertion portion 11. The image sensor is configured by, for example, a CCD (charge-coupled device) or a CMOS (complementary metal oxide semiconductor). Note that some of the components disposed at the distal end portion body 13 may be disposed in the operation portion 12.

The bending portion 14 of the insertion portion 11 is a first bending portion and configured to be bendable in a circumferential direction, which includes, for example, up-down and right-left directions (up (U)-down (D)/right (R)-left (L)), about an insertion axis.

The flexible tube portion 15 of the insertion portion 11 is configured by a tubular member having flexibility. The treatment instrument insertion channel 16, an image pickup cable, a light guide bundle, an air/water feeding tube, and the like, which are not illustrated, are disposed inside the flexible tube portion 15.

The treatment instrument insertion channel 16 is disposed from the distal end portion body 13 of the insertion portion 11 to the operation portion 12. The treatment instrument insertion channel 16 has a base end side opening 16a in a region on the distal end side of a predetermined position at which a bending operation portion 18 of the operation portion 12, which will be described later, is provided, and has a distal end side opening 16b at the distal end portion body 13 of the insertion portion 11.

A forceps valve 16c including, for example, a check valve (backflow prevention valve) is attached to the base end side opening 16a of the operation portion 12.

The treatment instrument insertion channel 16 allows insertion of an insertion portion 21 of the baby endoscope 20 as well as another treatment instrument or the like through the forceps valve 16c.

The bending operation portion 18 for performing a bending operation of the bending portion 14 is provided at a predetermined position on the base end side of the base end side opening 16a of the operation portion 12. The bending operation portion 18 includes a UD bending operation knob 18a, an RL bending operation knob 18b, a UD braking lever 18c, and an RL braking finger grip 18d.

Figure 2:
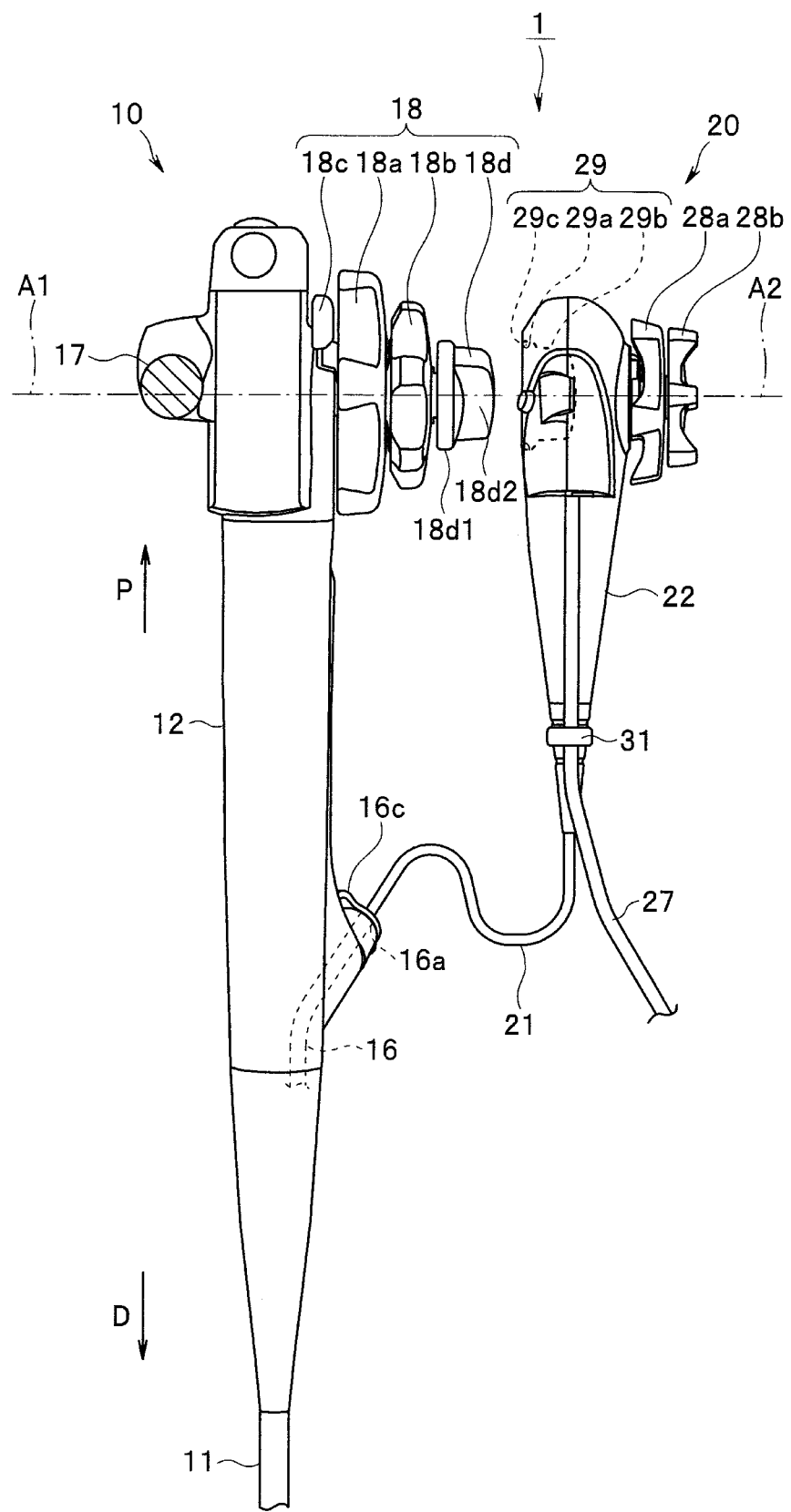
FIG. 2 is a side view illustrating a main part of the endoscope system before a baby endoscope is mounted onto a mother endoscope in Embodiment 1 described above.

The UD bending operation knob 18a, the RL bending operation knob 18b, the UD braking lever 18c, and the RL braking finger grip 18d are rotational operation members configured to be coaxially rotatable about a first central axis A1 (refer to FIG. 2 and the like).

The UD braking lever 18c, the UD bending operation knob 18a, the RL bending operation knob 18b, and the RL braking finger grip 18d are sequentially disposed along the first central axis A1 extending outward from a center side of the operation portion 12. Thus, the RL braking finger grip 18d is a member disposed on an outermost side of the bending operation portion 18.

The UD bending operation knob 18a is a rotational operation member for performing a bending operation of the bending portion 14 in the up-down direction such that the bending portion 14 bends in the U direction (up direction) when the UD bending operation knob 18a is rotated in one direction, and the bending portion 14 bends in the D direction (downward direction) when the UD bending operation knob 18a is rotated in the other direction.

The RL bending operation knob 18b is a rotational operation member for performing a bending operation of the bending portion 14 in the right-left direction such that the bending portion 14 bends in the R direction (right direction) when the RL bending operation knob 18b is rotated in one direction, and the bending portion 14 bends in the L direction (left direction) when the RL bending operation knob 18b is rotated in the other direction.

Bending in the circumferential direction about the insertion axis as described above can be performed by combining bending in the U-D direction by the UD bending operation knob 18a and bending in the R-L direction by the RL bending operation knob 18b.

The UD braking lever 18c is a member used to brake rotational operation of the UD bending operation knob 18a and configured to be displaced to a braking position at which rotation of the UD bending operation knob 18a is braked and to an open position at which rotation of the UD bending operation knob 18a is not braked.

The RL braking finger grip 18d is a member used to brake rotational operation of the RL bending operation knob 18b and configured to be displaced to a braking position at which rotation of the RL braking finger grip 18d is braked and to an open position at which rotation of the RL braking finger grip 18d is not braked.

The UD braking lever 18c and the RL braking finger grip 18d are configured to perform braking using, for example, frictional force and can control braking force at the braking positions. To achieve this, not only rotation of the UD braking lever 18c and the RL braking finger grip 18d can be restricted when the UD braking lever 18c and the RL braking finger grip 18d are moved to the braking positions, but also fine adjustment of rotational positions of the UD braking lever 18c and the RL braking finger grip 18d when the braking force is applied can be performed by slightly shifting the rotational positions.

A universal cable 17 is extended from a side part of the operation portion 12 on the base end side. An endoscope connector 17a is provided at an extension end of the universal cable 17. When the endoscope connector 17a is connected to an external instrument (such as a processor or a light source device), which is not illustrated, power, a drive signal, illumination light, and the like are supplied to the mother endoscope 10, and video picked up by the mother endoscope 10 is processed by the external instrument.

The baby endoscope 20 includes the insertion portion 21 that has an elongated shape and is insertable into the treatment instrument insertion channel 16 of the mother endoscope 10, and an operation portion 22 continuously provided on the base end side of the insertion portion 21. The baby endoscope 20 is a second endoscope, the insertion portion 21 is a second insertion portion, and the operation portion 22 is a second operation portion. Various operation members necessary for operating the baby endoscope 20 are disposed at the operation portion 22.

The insertion portion 21 is configured by a distal end portion body 23, a bending portion 24, and a flexible tube portion 25 continuously and sequentially provided from the distal end side toward the base end side.

Although not illustrated, for example, an LED light source (or a configuration in which illumination light from a light source device is transmitted through a light guide bundle) configured to generate illumination light, an illumination optical system configured to emit the generated illumination light, and an image pickup unit including an objective optical system and an image sensor are disposed at the distal end portion body 23 of the insertion portion 21. Similarly to the above description, the image sensor is configured by, for example, a CCD or a CMOS. Note that some of the components disposed at the distal end portion body 23 may be disposed in the operation portion 22.

The bending portion 24 of the insertion portion 21 is a second bending portion and configured to be bendable in the circumferential direction about the insertion axis, which includes, for example, up-down and right-left directions (U-D/R-L).

The flexible tube portion 25 of the insertion portion 21 is configured by a tubular member having flexibility. A treatment instrument insertion channel 26, an image pickup cable, an electrical power line for the LED light source, an air/water feeding tube, and the like, which are not illustrated, are disposed inside the flexible tube portion 25. The flexible tube portion 25 is configured to have a bending stiffness that is higher on the base end side than on the distal end side.

The treatment instrument insertion channel 26 is a second treatment instrument insertion channel disposed from the distal end portion body 23 of the insertion portion 21 to the operation portion 22. The treatment instrument insertion channel 26 has a base end side opening 26a at the operation portion 22 and has a distal end side opening, which is not illustrated, at the distal end portion body 23 of the insertion portion 21.

For example, a pipe sleeve 26b is provided at the base end side opening 26a of the operation portion 22.

The treatment instrument insertion channel 26 allows insertion of a treatment instrument or the like through the pipe sleeve 26b. The treatment instrument insertion channel 26 can also be used to inject contrast dye or the like.

A bending operation portion 28 for performing a bending operation of the bending portion 24 is provided on the base end side of the operation portion 22. The bending operation portion 28 is a second bending operation portion including a UD bending operation knob 28a, an RL bending operation knob 28b, and a braking lever 28c.

The UD bending operation knob 28a, the RL bending operation knob 28b, and the braking lever 28c are rotational operation members configured to be coaxially rotatable about a second central axis A2 (refer to FIG. 2 and the like).

The UD bending operation knob 28a is a rotational operation member for performing a bending operation of the bending portion 24 in the up-down direction such that the bending portion 24 bends in the U direction (up direction) when the UD bending operation knob 28a is rotated in one direction, and the bending portion 24 bends in the D direction (downward direction) when the UD bending operation knob 28a is rotated in the other direction.

The RL bending operation knob 28b is a rotational operation member for performing a bending operation of the bending portion 24 in the right-left direction such that the bending portion 24 bends in the R direction (right direction) when the RL bending operation knob 28b is rotated in one direction, or the bending portion 24 bends in the L direction (left direction) when the RL bending operation knob 28b is rotated in the other direction.

Bending in the circumferential direction about the insertion axis as described above can be performed by combining bending in the U-D direction by the UD bending operation knob 28a and bending in the R-L direction by the RL bending operation knob 28b.

The braking lever 28c is a member used to brake rotational operation of the UD bending operation knob 28a and the RL bending operation knob 28b and configured to be displaced to a braking position at which rotation of the UD bending operation knob 28a and the RL bending operation knob 28b is braked and to an open position at which rotation of the UD bending operation knob 28a and the RL bending operation knob 28b is not braked. The braking lever 28c is configured to perform braking using, for example, frictional force and as described above, not only rotation of the UD bending operation knob 28a and the RL bending operation knob 28b can be restricted by controlling the braking force, but also fine adjustment of rotational positions of the UD bending operation knob 28a and the RL bending operation knob 28b can be performed.

Cables and tubes 27 are extended from the base end side of the operation portion 22 (note that only one of the cables and tubes 27 is illustrated for simplification but a plurality of cables and tubes 27 may be provided). The cables and tubes 27 include cables for image pickup, power supply, and the like, air/water feeding tubes, and suction tubes and are connected with an external instrument (such as a processor or an air/water feeding device), which is not illustrated. The cables and tubes 27 are each locked to, for example, a brake prevention member of the operation portion 22 on the distal end side by a holder 31 such as a clip, a band or a strap.

A mounting portion for detachably mounting the operation portion 22 of the baby endoscope 20 onto the bending operation portion 18 is provided at the operation portion 22 as described above. In other words, a side of the operation portion 22 opposite to the bending operation portion 28 is a side of mounting onto the operation portion 12 of the mother endoscope 10. A concave portion 29 configured to receive an end part of the bending operation portion 18 is formed as the mounting portion at an exterior part of the operation portion 22 on the mounting side.

Figure 3:
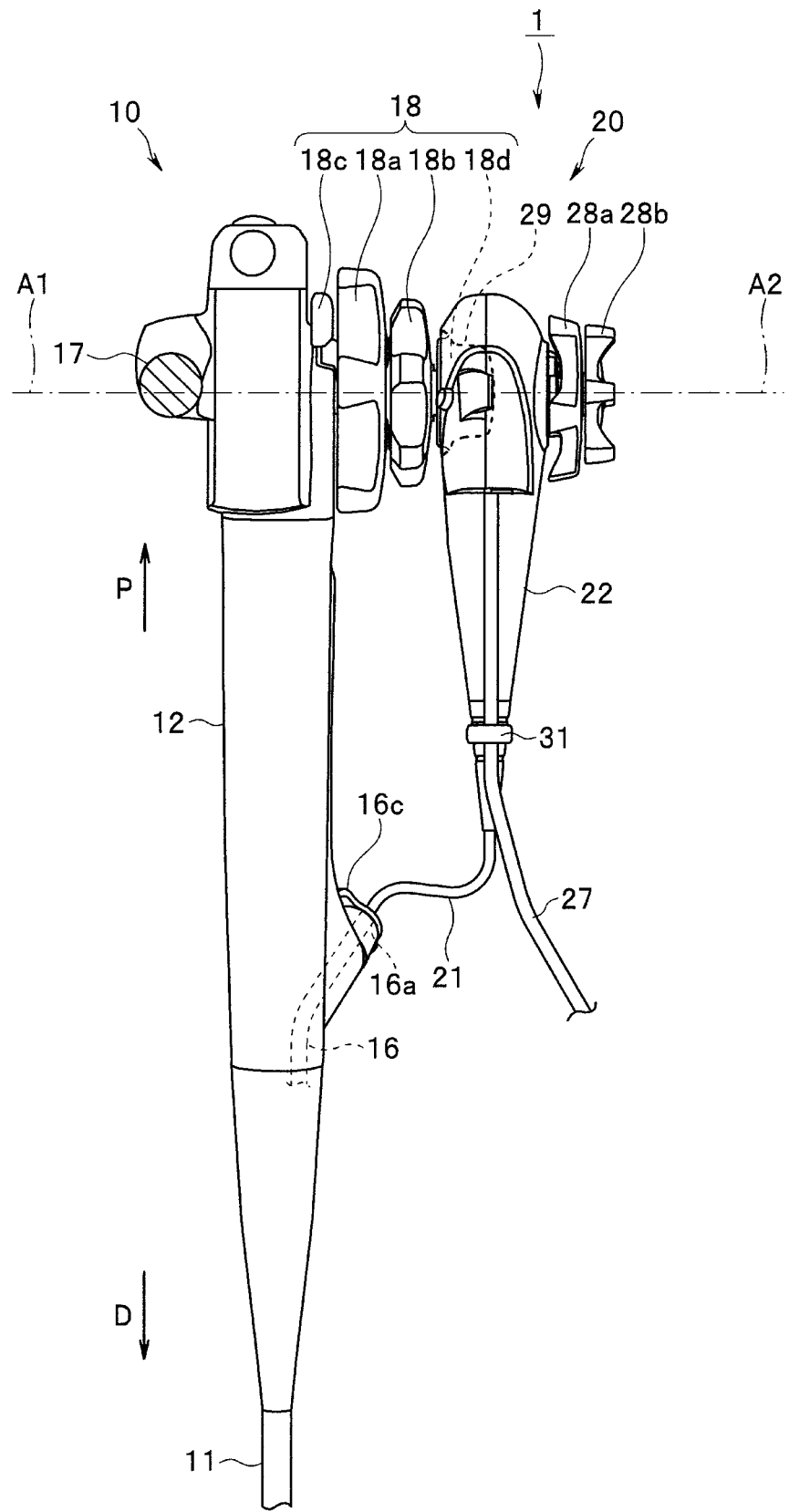
FIG. 3 is a side view illustrating the main part of the endoscope system after the baby endoscope is mounted onto the mother endoscope in Embodiment 1 described above.
Figure 4:
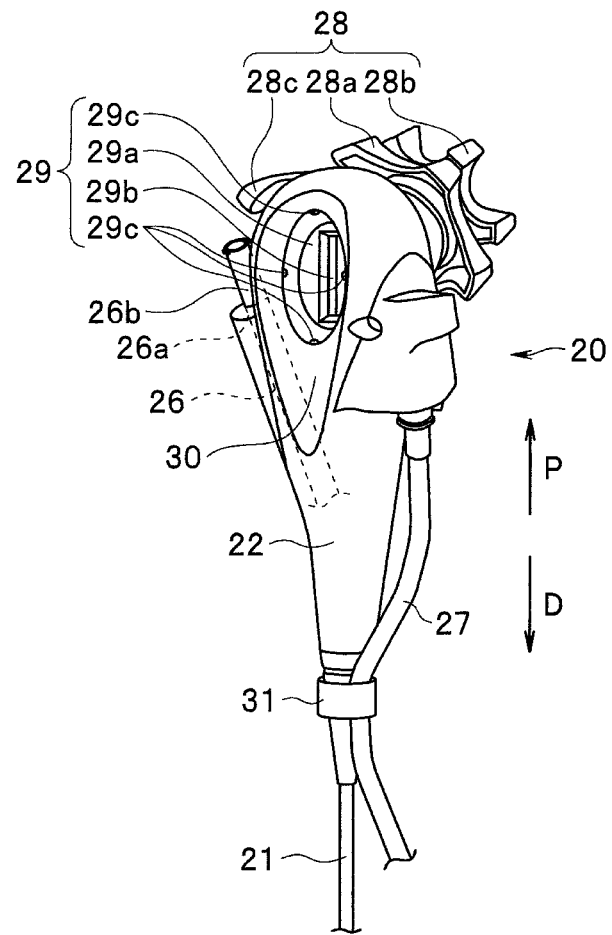
FIG. 4 is a perspective view illustrating a concave portion provided at an operation portion of the baby endoscope in Embodiment 1 described above.
Figure 5:
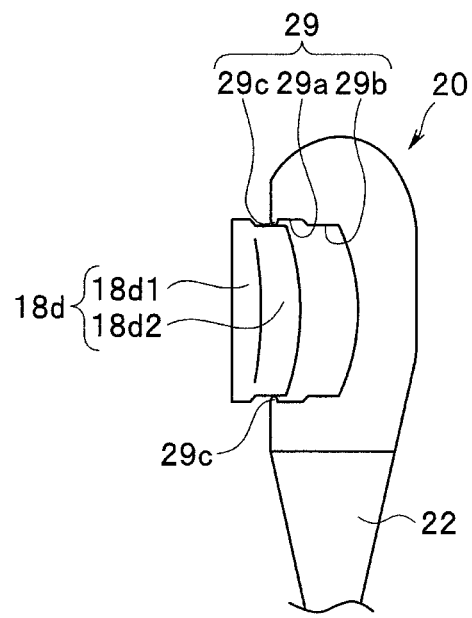
FIG. 5 is a diagram illustrating a shape of the concave portion provided at the operation portion of the baby endoscope in Embodiment 1 described above in comparison with a shape of an RL braking finger grip provided at the operation portion of the mother endoscope.

FIG. 2 is a side view illustrating a main part of the endoscope system 1 before the baby endoscope 20 is mounted onto the mother endoscope 10, FIG. 3 is a side view illustrating the main part of the endoscope system 1 after the baby endoscope 20 is mounted onto the mother endoscope 10, FIG. 4 is a perspective view illustrating the concave portion 29 provided at the operation portion 22 of the baby endoscope 20, and FIG. 5 is a diagram illustrating the shape of the concave portion 29 provided at the operation portion 22 of the baby endoscope 20 in comparison with the shape of the RL braking finger grip 18d provided at the operation portion 12 of the mother endoscope 10.

The RL braking finger grip 18d as a member disposed on the outermost side of the bending operation portion 18 of the mother endoscope 10 includes a disk portion 18d1, and a rectangular portion 18d2 protruding from the disk portion 18d1. The rectangular portion 18d2 has a rectangular shape (substantially rectangular parallelepiped shape) elongated in a radial direction of the disk portion 18d1.

The concave portion 29 of the operation portion 22 of the baby endoscope 20 is formed in a concave shape that fits an outer shape of the RL braking finger grip 18d. Specifically, the concave portion 29 includes a circular concave portion 29a having a concave shape that fits an outer shape of the disk portion 18d1, and a rectangular concave portion 29b provided on a bottom surface of the circular concave portion 29a and having a concave shape that fits an outer shape of the rectangular portion 18d2.

In particular, the concave portion 29 of the present embodiment is formed in, for example, a concave shape that fits the outer shape of the RL braking finger grip 18d at the braking position.

For example, when the mother endoscope 10 is inserted to a position at which a duodenal papilla can be observed and then only the baby endoscope 20 is inserted into a bile duct or the like through the duodenal papilla, the RL bending operation knob 18b is unlikely to be operated and the RL braking finger grip 18d is at the braking position.

Thus, the rectangular concave portion 29b of the baby endoscope 20 is formed in, for example, a concave shape that fits the outer shape of the rectangular portion 18d2 at the braking position.

In addition, the concave portion 29 includes a protrusion portion 29c for preventing dropping of the bending operation portion 18 as illustrated in FIGS. 4 and 5 and the like. The protrusion portions 29c are provided at, for example, a plurality of places on a periphery of an opening of the concave portion 29, such as the four places of upper, lower, right, and left places (alternatively, the protrusion portions 29c may be provided continuously (that is, in a ring shape) along the periphery of the opening of the concave portion 29).

As illustrated in FIG. 4, a gradually concave shape portion 30 for guiding the RL braking finger grip 18d to the concave portion 29 when the RL braking finger grip 18d is fitted to the concave portion 29 is formed around the concave portion 29.

Work is performed as follows when the baby endoscope 20 is mounted onto the mother endoscope 10.

First, the distal end portion body 23 of the insertion portion 21 of the baby endoscope 20 is placed in the base end side opening 16a of the treatment instrument insertion channel 16 of the mother endoscope 10 and further inserted so that substantially the entire length of the insertion portion 21 is housed in the treatment instrument insertion channel 16.

After the insertion portion 21 is substantially housed in the treatment instrument insertion channel 16, the concave portion 29 of the operation portion 22 of the baby endoscope 20 is placed closer to the RL braking finger grip 18d of the bending operation portion 18 of the mother endoscope 10.

In this case, once the RL braking finger grip 18d contacts the concave shape portion 30 even when the concave portion 29 does not precisely face the RL braking finger grip 18d, the RL braking finger grip 18d is guided to the concave portion 29 along a curved surface shape of the concave shape portion 30.

Then, after the concave portion 29 faces the RL braking finger grip 18d, the concave portion 29 is placed closer to the RL braking finger grip 18d in a direction of the first central axis A1. Accordingly, the rectangular portion 18d2 of the RL braking finger grip 18d starts entering the concave portion 29, and the disk portion 18d1 contacts the protrusion portions 29c when the rectangular portion 18d2 is housed in the concave portion 29.

When pressing force is further applied in this state, the disk portion 18d1 starts entering the concave portion 29 against reaction force of the protrusion portions 29c, and the RL braking finger grip 18d is entirely housed in the concave portion 29 as pressing is further continued. In this case, the protrusion portions 29c prevent the RL braking finger grip 18d from dropping off the concave portion 29.

When the operation portion 22 of the baby endoscope 20 is mounted on the bending operation portion 18 of the mother endoscope 10 as described above in this manner, it is preferable that the first central axis A1 and the second central axis A2 be parallel to each other and an interaxial distance (distance between A1 and A2 in a plane orthogonal to the axes) is short. It is further preferable that the first central axis A1 and the second central axis A2 be coaxial.

Thus, the concave portion 29 as the mounting portion in the present embodiment is disposed at such a position that the first central axis A1 and the second central axis A2 are, for example, coaxial when the operation portion 22 is mounted on the bending operation portion 18.

To prevent the base end side of the insertion portion 21 of the baby endoscope 20 from bending at a small curvature, the operation portion 22 of the baby endoscope 20 may be formed in a size and a shape with which a distal end of the operation portion 22 (more specifically, a distal end of the brake prevention member of the operation portion 22) is positioned on the base end side of the base end side opening 16a of the treatment instrument insertion channel 16 when the baby endoscope 20 is mounted on the mother endoscope 10 (refer to FIG. 2 and the like).

When the endoscope system 1 in which the baby endoscope 20 is mounted on the mother endoscope 10 is operated, the mother endoscope 10 is inserted or removed with the operation portion 12 being grasped in a left hand and the insertion portion 11 being held in a right hand. In addition, a button, a lever, and the like disposed at the operation portion 12 are operated by fingers of the left hand grasping the operation portion 12. The operation portion 22 of the baby endoscope 20 can be operated by, for example, the right hand.

The operation portion 22 of the baby endoscope 20 can be operated by fingers of the left hand grasping the operation portion 12 when a thickness of the mother endoscope 10 in the direction of the first central axis A1 and a thickness of the baby endoscope 20 in the direction of the second central axis A2 are appropriately designed. In this case, operability of the endoscope system 1 by one person can be further improved.

To remove the baby endoscope 20 from the mother endoscope 10, the above-described mounting work procedure may be performed in a substantially reverse order.

Specifically, when tensile force that separates the operation portion 22 of the baby endoscope 20 from the RL braking finger grip 18d in the direction of the first central axis A1 is applied against locking force by the protrusion portions 29c, the disk portion 18d1 moves over the protrusion portions 29c and becomes separated. As the separation is further performed, the operation portion 22 is moved to a position at which the RL braking finger grip 18d is not housed in the concave portion 29. Thereafter, the insertion portion 21 of the baby endoscope 20 can be removed from the treatment instrument insertion channel 16 of the mother endoscope 10.

Note that although the configuration in which the concave portion 29 of the baby endoscope 20 is fitted to the RL braking finger grip 18d as a convex portion of the mother endoscope 10 is employed in the above description, the concave and convex portions may be interchanged to employ a configuration in which a convex portion of the baby endoscope 20 is fitted to a concave portion of the mother endoscope 10. Moreover, the configuration of the mounting portion is not limited to fitting of a pair of concave and convex portions, but for example, the operation portion 22 of the baby endoscope 20 may be fixed to the bending operation portion 18 of the mother endoscope 10 by a band, a strap, or the like.

Although the above description is made on the example in which the bending operation portion 18 is of a rotational operation type, the bending operation portion 18 may be of a joystick type or a slide type in place of the rotational operation type.

According to Embodiment 1 as described above, operability of the baby endoscope 20 in a state of grasping the operation portion 12 of the mother endoscope 10 is improved so that the mother-baby endoscope system 1 can be operated by one person.

Specifically, since the operation portion 22 of the baby endoscope 20 as the medical device is detachably mounted on the bending operation portion 18 of the mother endoscope 10, the operation portion 12 and the operation portion 22 are positioned close to each other so that the operation portion 12 and the operation portion 22 are at substantially the same positions in a direction of the insertion axis, in particular, and thus the operability is improved. Moreover, when shapes and sizes of the operation portion 12 of the mother endoscope 10 and the operation portion 22 of the baby endoscope 20 are appropriately designed, the operation portion 22 of the baby endoscope 20 can be operated by fingers of the left hand grasping the operation portion 12, and thus the operability by one person can be further improved.

Since the base end side opening 16a of the treatment instrument insertion channel 16 is positioned on the distal end side of the bending operation portion 18, the insertion portion 21 of the baby endoscope 20 can be inserted into the treatment instrument insertion channel 16 of the mother endoscope 10 without looping. Thus, the insertion portion 21 of the baby endoscope 20 can be shortened, and in addition, a treatment instrument that is inserted into the treatment instrument insertion channel 26 of the baby endoscope 20 is not limited to a long one, and accordingly, the number of kinds of applicable treatment instrument increases.

Since the mounting portion is the concave portion 29 configured to receive the end part of the bending operation portion 18, the baby endoscope 20 can be easily mounted onto the mother endoscope 10 by one action without an additional member such as a band or a strap.

Since the concave portion 29 is formed in a concave shape that fits the outer shape of the RL braking finger grip 18d, influence on operability of the mother endoscope 10 can be reduced. Specifically, the RL braking finger grip 18d and the RL bending operation knob 18b of the mother endoscope 10 are hardly used when the baby endoscope 20 is mounted on the mother endoscope 10, and thus the operability of the mother endoscope 10 hardly decreases.

Since the concave portion 29 is formed in a concave shape that fits the outer shape of the RL braking finger grip 18d at the braking position, the bending portion 14 of the mother endoscope 10 can be prevented from unintentionally bending to right and left when the baby endoscope 20 is operated.

Since the protrusion portions 29c are provided at the concave portion 29, the operation portion 22 of the baby endoscope 20 can be prevented from unintentionally dropping off the operation portion 12 of the mother endoscope 10.

Since the first central axis A1 of the bending operation portion 18 of the mother endoscope 10 and the second central axis A2 of the bending operation portion 28 of the baby endoscope 20 are coaxial (or substantially coaxial) when the baby endoscope 20 is mounted on the mother endoscope 10, the operation portion 22 of the baby endoscope 20 can be operated as an extension of the operation portion 12 of the mother endoscope 10, and thus the operability can be further improved.

Since the medical device is the baby endoscope 20 including the treatment instrument insertion channel 26, it is possible not only to perform object observation by the baby endoscope 20 but also to perform treatment with a treatment instrument while performing the observation.

In a conventional technology in which the baby endoscope 20 is mounted on, for example, the brake prevention member of the mother endoscope 10, when a twisting operation of the mother endoscope 10 being grasped in the left hand is performed, the mother endoscope 10 needs to be tilted in addition to the twisting so that the right hand can easily reach the operation portion 22 of the baby endoscope 20. Thus, such a difficult operation of tilting the left hand being twisted is needed and thus the operability decreases. However, with a configuration of the present embodiment, the mother endoscope 10 does not need to be tilted, and accordingly, the operability improves.

In a conventional technology in which the baby endoscope 20 is attached to, for example, the brake prevention member of the mother endoscope 10 by using a band, a strap, or the like, a position of the baby endoscope 20 around the insertion axis relative to the mother endoscope 10 changes in some cases. However, with the configuration of the present embodiment, since the baby endoscope 20 is mounted on the bending operation portion 18 of the mother endoscope 10, the position of the baby endoscope 20 around the insertion axis relative to the mother endoscope 10 does not change, and a positional relation between the operation portion 12 and the operation portion 22 is maintained constant. Thus, it is possible to operate the baby endoscope 20 without visually recognizing a positional relation between the baby endoscope 20 and the mother endoscope 10.

Embodiment 2

Figure 6:
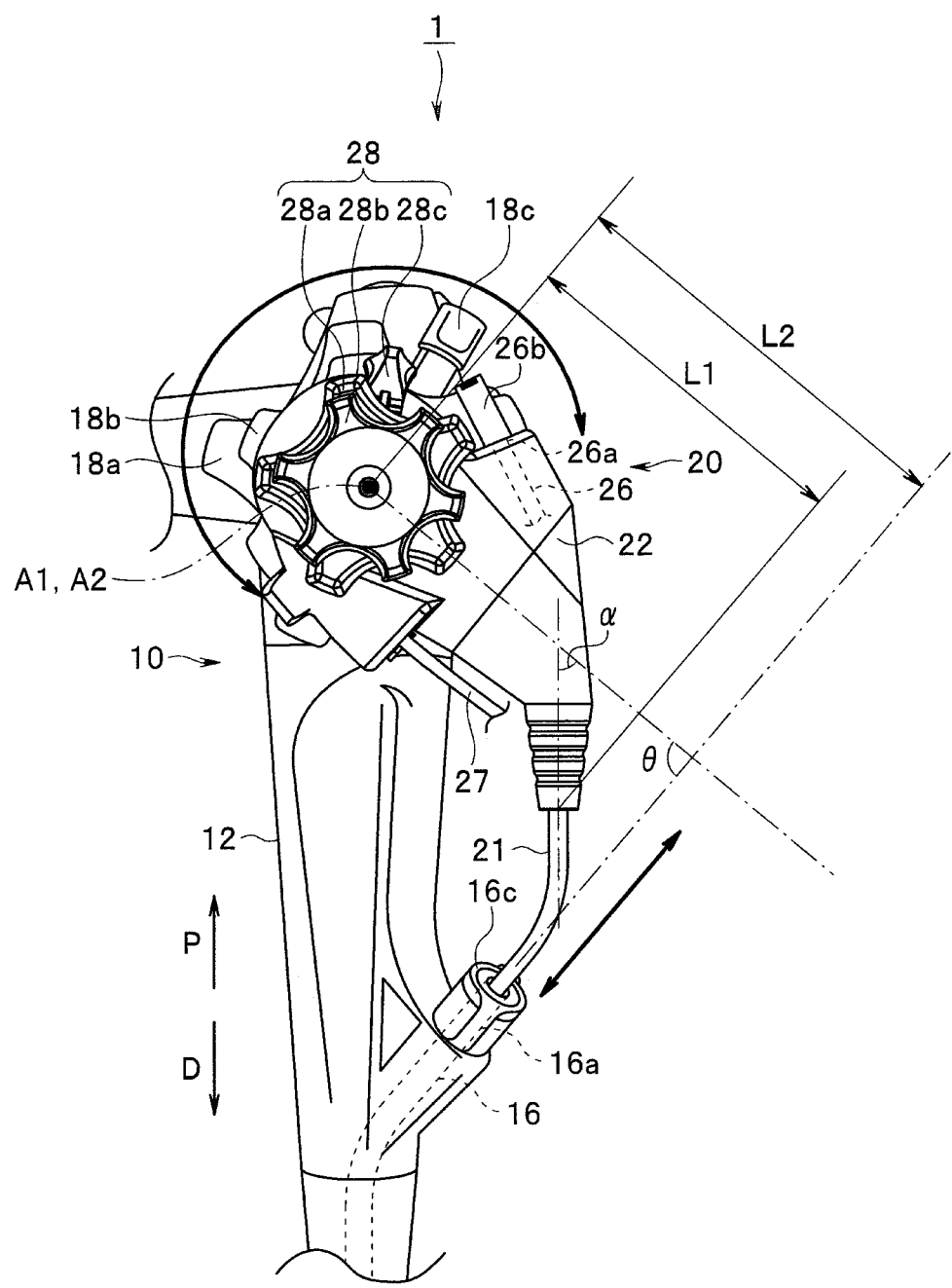
FIG. 6 is a side view illustrating a situation in which an insertion length of an insertion portion of the baby endoscope mounted on the mother endoscope in Embodiment 2 of the present invention is changed.

FIG. 6 illustrates Embodiment 2 of the present invention and is a side view illustrating a situation in which an insertion length of the insertion portion 21 of the baby endoscope 20 mounted on the mother endoscope 10 is changed.

In Embodiment 2, a component same as a component in Embodiment 1 described above is, for example, denoted by an identical reference sign and omitted from description as appropriate, and only any difference will be mainly described.

In the present embodiment, the baby endoscope 20 is configured to be rotatable about the first central axis A1 when mounted on the mother endoscope 10, and the insertion length of the insertion portion 21 is changed by rotating the baby endoscope 20. Note that although FIG. 6 illustrates an example in which the first central axis A1 and the second central axis A2 are coaxial, description below is also applicable to a case in which the axes are not coaxial.

Similarly to Embodiment 1 described above, the baby endoscope 20 is mounted on the mother endoscope 10 when the concave portion 29 of the baby endoscope 20 is fitted to the RL braking finger grip 18*d* of the mother endoscope 10.

Thus, the RL braking finger grip 18*d* is rotated when the baby endoscope 20 is rotated about the first central axis A1 while the rectangular concave portion 29*b* and the rectangular portion 18*d*2 are fitted to each other.

A circular concave portion may be formed in place of the rectangular concave portion 29*b*, and in this case, the RL braking finger grip 18*d* is not rotated when the baby endoscope 20 is rotated about the first central axis A1.

Only with the circular concave portion formed in place of the rectangular concave portion 29*b*, it is difficult to hold a rotational position of the baby endoscope 20 when the baby endoscope 20 is rotated about the first central axis A1. Thus, for example, a frictional member (such as an O-shaped ring configured by rubber or the like) configured to generate appropriate frictional force may be provided at the concave portion 29 so that the baby endoscope 20 can be rotated against the frictional force, and the RL braking finger grip 18*d* is not rotated when the baby endoscope 20 is rotated, but when the rotation of the baby endoscope 20 is stopped, the baby endoscope 20 is locked by the frictional force at the current rotational position. In this case, the O-shaped ring or the like may also function as the protrusion portions 29*c*. Thus, the O-shaped ring may be configured as, for example, a plurality of rubber protrusion portions.

Note that a configuration for holding the rotational position of the baby endoscope 20 is not limited to the configuration described above, but another appropriate configuration may be employed.

In the baby endoscope 20 of Embodiment 1 described above, an axial direction of the operation portion 22 and an extension direction of the insertion portion 21 from the operation portion 22 are the same. However, the baby endoscope 20 of the present embodiment is configured so that the axial direction of the operation portion 22 and the extension direction (axial direction of the brake prevention member) of the insertion portion 21 from the operation portion 22 have a predetermined angle $\alpha$ ($0° \leq \alpha \leq 90°$) as illustrated in FIG. 6.

The predetermined angle $\alpha$ is preferably close to 90° as much as possible in a range of restriction by internal components of the insertion portion 21, such as the treatment instrument insertion channel 26, a cable, and a tube.

A length of the operation portion 22 in an axial direction to the distal end side from a starting point at the first central axis A1 is denoted by L1. In addition, a distance between an extended straight line of a channel central axis of the treatment instrument insertion channel 16 at the base end side opening 16*a* and the first central axis A1 is denoted by L2. In this case, the baby endoscope 20 is designed and manufactured so that the operation portion 22 satisfies L1<L2.

An angle between an extended straight line of the axial direction of the operation portion 22 and the extended straight line of the channel central axis of the treatment instrument insertion channel 16 at the base end side opening 16*a* is denoted by $\theta$ (note that when the two straight lines are at twisted positions, an angle between straight lines obtained by projecting the two straight lines onto a plane orthogonal to the first central axis A1 is denoted by $\theta$).

In this case, as the operation portion 22 is rotated anticlockwise in FIG. 6, the angle $\theta$ decreases and the insertion portion 21 is somewhat removed from the base end side opening 16*a*, in other words, the insertion length of the insertion portion 21 reduces.

As the operation portion 22 is rotated clockwise in FIG. 6, the angle $\theta$ increases and the insertion portion 21 is somewhat inserted into the base end side opening 16*a*, in other words, the insertion length of the insertion portion 21 increases.

Since the configuration satisfies L1<L2 as described above when such adjustment of the insertion length of the insertion portion 21 is performed by rotating the operation portion 22, it is possible to prevent buckling of the base end side of the insertion portion 21.

Moreover, since the insertion portion 21 of the baby endoscope 20 is configured to have a bending stiffness that is higher on the base end side than on the distal end side as described above, it is possible to more effectively prevent buckling.

According to Embodiment 2 as described above, effects substantially the same as effects of Embodiment 1 described above can be achieved, and it is also possible to adjust a position of the distal end portion body 23 of the insertion portion 21 through a simple operation of rotating the operation portion 22 since the concave portion 29 is formed in a shape that allows rotation of the operation portion 22 relative to the operation portion 12 so that the insertion length of the insertion portion 21 is changed by rotating the operation portion 22.

When the shapes and sizes of the operation portion 12 and the operation portion 22 are appropriately designed, it is possible to rotate the operation portion 22 by fingers of the left hand grasping the operation portion 12 and adjust the position of the distal end portion body 23 of the insertion portion 21 while the insertion portion 11 of the mother endoscope 10 is held in the right hand. In this manner, the operability when the endoscope system 1 is operated by one person can be improved, and thus it is possible to more stably perform an endoscopic procedure.

Note that the present invention is not limited to the above-described embodiments but components of the present invention may be modified and materialized without departing from the gist of the present invention when performed. Moreover, various kinds of aspects of the invention may be formed appropriately combining a plurality of components disclosed in the above-described embodiments. For example, some components indicated in the embodiments may be deleted. In addition, components in different embodiments may be combined as appropriate. In this manner, various kinds of modifications and applications are possible without departing from the scope of the invention.

What is claimed is:

1. A medical device comprising:
   an operation portion;
   an insertion portion provided on a distal end side of the operation portion;
   a channel provided from the operation portion to the insertion portion; and
   a mounting portion configured to detachably mount onto an outer surface of a bending operation member of a first endoscope.

2. The medical device according to claim 1, wherein the mounting portion comprises an exterior surface of the operation portion, the exterior surface having a concavity configured to receive a projecting portion of the outer surface of the bending operation member of the first endoscope.

3. The medical device according to claim 2, wherein the bending operation member of the first endoscope includes a bending operation knob for performing a bending operation of an insertion portion of the first endoscope, and a braking finger grip for braking operation of the bending operation knob, the braking finger grip having the projecting portion, and
the concavity having a shape that matingly engages with the projecting portion of the braking finger grip.

4. The medical device according to claim 3, wherein the braking finger grip is configured to be switched between a braking position and an open position, at the braking position, the braking finger grip is configured to brake an operation of the bending operation knob, and at the open position, the braking finger grip is configured to allow the operation of the bending operation knob, and
the concavity matingly engages with the projecting portion of the braking finger grip when the braking finger grip is at the braking position.

5. The medical device according to claim 2, wherein the concavity having a shape that allows rotation of the operation portion relative to an operation portion of the first endoscope when the mounting portion is mounted onto the outer surface of the bending operation member of the first endoscope, and
a length of insertion of the insertion portion into a treatment instrument insertion channel of the first endoscope is changed by rotating the operation portion relative to the operation portion of the first endoscope.

6. The medical device according to claim 2, wherein the concavity further includes a protrusion for retaining the bending operation member of the first endoscope in the concavity.

7. The medical device according to claim 2, wherein the concavity has a first central axis, and
the operation portion is configured to rotate about a second central axis, and
the first central axis and the second central axis are coaxial.

8. The medical device according to claim 2, wherein the concavity has a first concave portion and a second concave portion, and
the first concave portion has a first shape and the second concave portion has a second shape that is different from the first shape.

9. The medical device according to claim 1, wherein the bending operation member of the first endoscope is operated to rotate about a first central axis,
the insertion portion includes a medical device bending portion,
the operation portion includes a medical device bending operation portion for performing a bending operation of the medical device bending portion, the medical device bending operation portion being configured to be operated to rotate about a second central axis, and
the mounting portion is configured so that the first central axis and the second central axis are coaxial when the mounting portion is mounted on the bending operation member of the endoscope.

10. The medical device according to claim 1, wherein the medical device is a second endoscope, and
the channel is a treatment instrument insertion channel.

11. The medical device according to claim 1, wherein the operation portion includes an operation member and the mounting portion comprises a concavity provided on a first position opposed to a second position of the operation member relative to a longitudinal axis of the operation portion.

12. The medical device according to claim 1, wherein the insertion portion includes a distal insertion portion and a proximal insertion portion provided proximally relative to the distal insertion portion, and
the distal insertion portion has a first bending stiffness and the proximal insertion portion has a second bending stiffness that is higher than the first bending stiffness.

13. An endoscope system comprising:
a first endoscope; and
a medical device attachable to the first endoscope, wherein
the first endoscope comprises:
 a first operation portion,
 a first insertion portion including a first bending portion, the first insertion portion being and continuously provided on a distal end side of the first operation portion,
 wherein the first operation portion comprises a first bending operation member configured to perform a bending operation of the first bending portion, and
 a treatment instrument insertion channel provided in the first insertion portion and the first operation portion, the treatment instrument insertion channel having a base end side opening at the first operation portion and a distal end side opening at a distal end portion of the first insertion portion, and
the medical device comprises:
 a second operation portion,
 a second insertion portion that is continuously provided on the distal end side of the second operation portion, the second insertion portion being configured to be inserted into the treatment instrument insertion channel,
 a channel provided from the second operation portion to the second insertion portion, and
 wherein the second operation portion comprises a mounting portion configured to detachably mount onto an outer surface of the first bending operation member.

14. The endoscope system according to claim 13, wherein the mounting portion is configured to prevent a manual input to the first bending operation member when the mounting portion is mounted onto the outer surface of the first bending operation member.

15. The medical device according to claim 13, wherein the first bending operation member includes a bending operation knob and a braking finger grip configured to prevent the first bending operation member from rotating, and
the mounting portion comprises a concavity, at least a portion of the concavity is configured to matingly engage with an outer surface of the braking finger grip.

16. The medical device according to claim 13, wherein the first bending operation member includes a bending operation knob and a braking finger grip configured to be moved between a braking position and an open position, at the braking position, the braking finger grip is configured to brake an operation of the bending operation knob, and at the open position, the braking finger grip is configured to allow the operation of the bending operation knob, and the mounting portion comprises a concavity configured to matingly engage with an outer shape of the braking finger grip when the braking finger grip is at the braking position.

17. The medical device according to claim 13, wherein the mounting portion comprises a concavity configured to receive at least a portion of the outer surface of the first bending operation member and to allow rotation of the second operation portion relative to the first operation portion, and a length of insertion of the second insertion portion into the treatment instrument insertion channel is changed by rotating the second operation portion relative to the first operation portion.

18. The medical device according to claim 13, wherein the mounting portion comprises a concavity configured to receive a part of the outer surface of the first bending operation member, and the concavity includes a protrusion for retaining the first bending operation member in the concavity.

19. The medical device according to claim 13, wherein the second insertion portion includes a distal insertion portion and a proximal insertion portion provided proximally relative to the distal insertion portion, and the distal insertion portion has a first bending stiffness and the proximal insertion portion has a second bending stiffness that is higher than the first bending stiffness.

20. The medical device according to claim 13, wherein the second operation portion includes a concavity configured to receive a part of the outer surface of the first bending operation member, the concavity has a first concave portion and a second concave portion, and the first concave portion has a first shape and the second concave portion has a second shape that is different from the first shape.

\* \* \* \* \*